US005283823A

United States Patent [19]

Morris

[11] Patent Number: 5,283,823

[45] Date of Patent: Feb. 1, 1994

[54] PORTABLE RADIOGRAPHIC DEVICE

[75] Inventor: William W. Morris, Woodstock, Ill.

[73] Assignee: X-Cel X-Ray Corporation, Crystal Lake, Ill.

[21] Appl. No.: 944,496

[22] Filed: Sep. 14, 1992

Related U.S. Application Data

[63] Continuation-in-part of Ser. No. 800,154, Nov. 27, 1991, abandoned.

[51] Int. Cl.[5] .......... A61B 6/10

[52] U.S. Cl. .......... 378/198; 378/193; 378/196

[58] Field of Search .......... 378/196, 198, 193, 197

[56] References Cited

U.S. PATENT DOCUMENTS

| | | | |
|---|---|---|---|
| D. 273,892 | 5/1984 | Fenne et al. | D24/2 |
| D. 291,916 | 9/1987 | Davis | D24/2 |
| 1,184,503 | 5/1916 | Alden . | |
| 1,239,145 | 9/1917 | Wantz | 378/198 |
| 1,913,695 | 6/1933 | Werner . | |
| 3,801,790 | 4/1974 | Götzl et al. | 378/198 |
| 4,223,230 | 9/1980 | Waerve et al. | 378/198 |
| 4,326,131 | 4/1982 | Waerve | 378/198 |
| 4,335,315 | 6/1982 | Waerve et al. | 378/198 |
| 4,577,340 | 3/1986 | Carlson et al. | 378/132 |
| 4,590,378 | 5/1986 | Platz | 250/363 |
| 4,694,480 | 9/1987 | Skillicorn | 378/119 |
| 4,752,948 | 6/1988 | MacMahon | 378/198 |
| 4,775,994 | 10/1988 | Kranvogel | 378/197 |
| 4,887,287 | 12/1989 | Cobben | 378/197 |
| 4,964,151 | 10/1990 | Trotel | 378/198 |
| 4,989,229 | 1/1991 | Negrelli et al. | 378/198 |
| 5,081,662 | 1/1992 | Warden et al. | 378/196 |

OTHER PUBLICATIONS

Porta Ray Model No. 9160 brochure (late 1989).
Porta Ray Model No. 9170 brochure (late 1989).
Dynarad Model No. HF-110 advertisement (dated Aug. 15, 1991).
Minxray, Inc. Model No. H500 advertisement (late 1990).
Kramex Model No. PX-40H brochure (late 1988).
X-Cel X-Ray Corporation brochure (early 1991).

*Primary Examiner*—David P. Porta
*Assistant Examiner*—Don Wong
*Attorney, Agent, or Firm*—Marshall, O'Toole, Gerstein, Murray & Borun

[57] ABSTRACT

A mobile, radiographic unit which includes a wheel mounted base assembly and a roll bar assembly connected to the base. A vertical column is disposed on the base and a carriage assembly travels along the column length. Arm extension members extend outward from the carriage with a radiographic head being connected to the arm extensions by a disconnect assembly. Separate means are employed for maintaining the carriage assembly in a selected position relative to the column and maintaining the arm extension members in selected position relative to the carriage assembly.

27 Claims, 9 Drawing Sheets

111 22 20 24 25 26 64 28 10 77 71 90 28 62 110 63 16 14 70 60 82 151 150 103 107 87 88 E 91 73 72 78 12 57 33 55 52a 39

111
22
20
10
25
24
73
71
26
61
28
87
60
52a
110
16
39
82
70
63
62
103
107
75
73
72
12
55
57

111
120
22
123
121
111
18
126
124
20
134
68
24
25
67
64
26
65
89
88
10
70
61
112
98
112
62
110
110
28
60
16
100
82
65
39
38
83
88
89
14
91
91
73
72
76
75
78
78
35
74
33
57
52b
12
52a
57

301
299
302
220
224
C
C
308
309
310
322
267
268
295
290
276
291
322
292
272
321
373
374
320
210
278
277
261
265
266
305
303
271
238
240
242
241
275
253
233
243
13
13
252B
232
284
283
255
F

PORTABLE RADIOGRAPHIC DEVICE

CROSS-REFERENCE TO RELATED APPLICATION

This application is a continuation-in-part application of my pending application Ser. No. 07/800,154 filed Nov. 27, 1991, now abandment.

FIELD OF INVENTION

The invention relates generally to portable radiographic equipment, and more particularly to equipment for providing relatively easy transportation and storage of x-ray equipment including the assembly of the equipment from a collapsed, inoperative position to an open, operative position for taking radiographs.

BACKGROUND OF THE INVENTION

It is well known to have portable units for radiography, however, in many instances, the units have been found to be less than satisfactory. In some instances, it has been found that portable x-ray units must be disassembled into individual components which are then subsequently reassembled at another site, a time consuming procedure requiring installation tools and teaching an operator the details of the assembly procedure.

In other instances, it has been found that, while a portable x-ray unit can be collapsed into an inoperative position, problems arise in the storage and/or transporting of the unit. Specifically, when the unit is collapsed, it only has one storage position which often is undesirable particularly if a unit has to be stored under a bed or table. Further, when the portable x-ray unit is transported from one job site to another, a concern exists that various components can be damaged in the course of transportation because the components are exposed to other elements with the attendant consequence that the unit can be severely damaged.

It has also been observed that with portable radiographic units presently available, a problem exists in that the unit is not operator friendly with respect to readily and easily positioning the unit relative to an examining table or the like on which a patient is placed for radiographic purposes. In many instances, it is necessary for an operator to negotiate the portable unit into a desired position relative to the table and patient for taking the x-rays. In carrying out this alignment procedure, it is sometimes necessary for the operator to stand on either side of the examining table or patient while placing the radiographic unit in proper position. It can be very difficult for an operator to stand on one side of a table or patient opposite the side where the unit is located and attempt to move the unit by reaching over the table or patient to grasp the unit and move it to a desired position.

What is desired is to have a relatively lightweight, portable radiographic device in which the x-ray head can be positioned in a desired open, operative position relative to a patient to be x-rayed. It is also desired that the unit be adapted to be placed in either an open, operative position for radiography or an inoperative, collapsed position so that the unit can be relatively easily transported and/or stored. Further, it is desired that when the unit is in a collapsed position, various components be protected from contacting other elements so that the unit will not be damaged in transit from one location to another or while it is in storage. It also is desired that the unit have more than one position in which it can be safely and conveniently stored.

Finally, it is desired to have a portable x-ray unit which can be positioned in a desired location relative to an examining table or patient whereby an operator can orient the unit relative to the table or patient irrespective of the side of the table or patient where the operator is positioned.

SUMMARY OF THE INVENTION

The invention disclosed and claimed herein serves to overcome or otherwise obviate the above-described problems presently existing with portable radiographic units.

Briefly, the portable radiographic unit of the present invention is a relatively compact unit which utilizes a base assembly upon which is disposed a vertical column assembly. A movable carriage assembly is connected to the column assembly and is adapted to travel vertically along he length of the column assembly. A pair of pivotable arm extension members extend outward from the carriage assembly. An x-ray head, which includes a power source and collimator, depends from and is releasably connected to a disconnectable assembly located at the outboard ends of the arm extension members.

In one embodiment of the present invention, a first counterbalancing means is employed to selectively position the carriage in a desired position relative to the column assembly and a second counterbalancing means is utilized to selectively position the arm extension members and x-ray head relative to the carriage assembly.

In a second embodiment of the invention, the carriage assembly is attached to a carriage mount adapted to travel vertically along a screw track disposed within the column assembly whereby the carriage assembly is selectively positioned in a desired position relative to the column assembly. A piston assembly attached to the carriage assembly has a piston rod which is indirectly connected at its distal end to the pivotable arm extension members. The piston rod can be adjustably positioned from a closed to an extended position such that the x-ray head is selectively positioned in an open, operative position or a closed, inoperative position.

The radiographic unit further includes a protective roll oar assembly means for protecting the unit when it is transported, and, further, for allowing the unit to be stored in a number of positions without damage to the various components of the unit. The roll bar assembly includes a pair of spaced inverted U-shaped rail members attached to the base assembly If desired, for additional reinforcement and protection purposes, cross bars can extend across the inverted U-shaped sections. When the unit is in a collapsed, inoperative position, various components are disposed within the confines of the spaced rails which serve to protect the components from damage during transportation and/or storage.

The unit also is operator friendly because the rail members allow an operator to easily grasp the rails while orienting the radiographic unit relative to an x-ray table, patient or the like irrespective of what side of a table or patient the operator is standing in the unit/-patient orientation procedure. The vertical legs of the rail members act as a positioning stop for orienting the radiographic unit relative to the centerline of a patient on an x-ray table.

DESCRIPTION OF THE DRAWINGS

Further advantages of the invention will become apparent upon a reading of the following detailed description taken in conjunction with the accompanying drawings in which.

DETAILED DESCRIPTION

Figure 1:
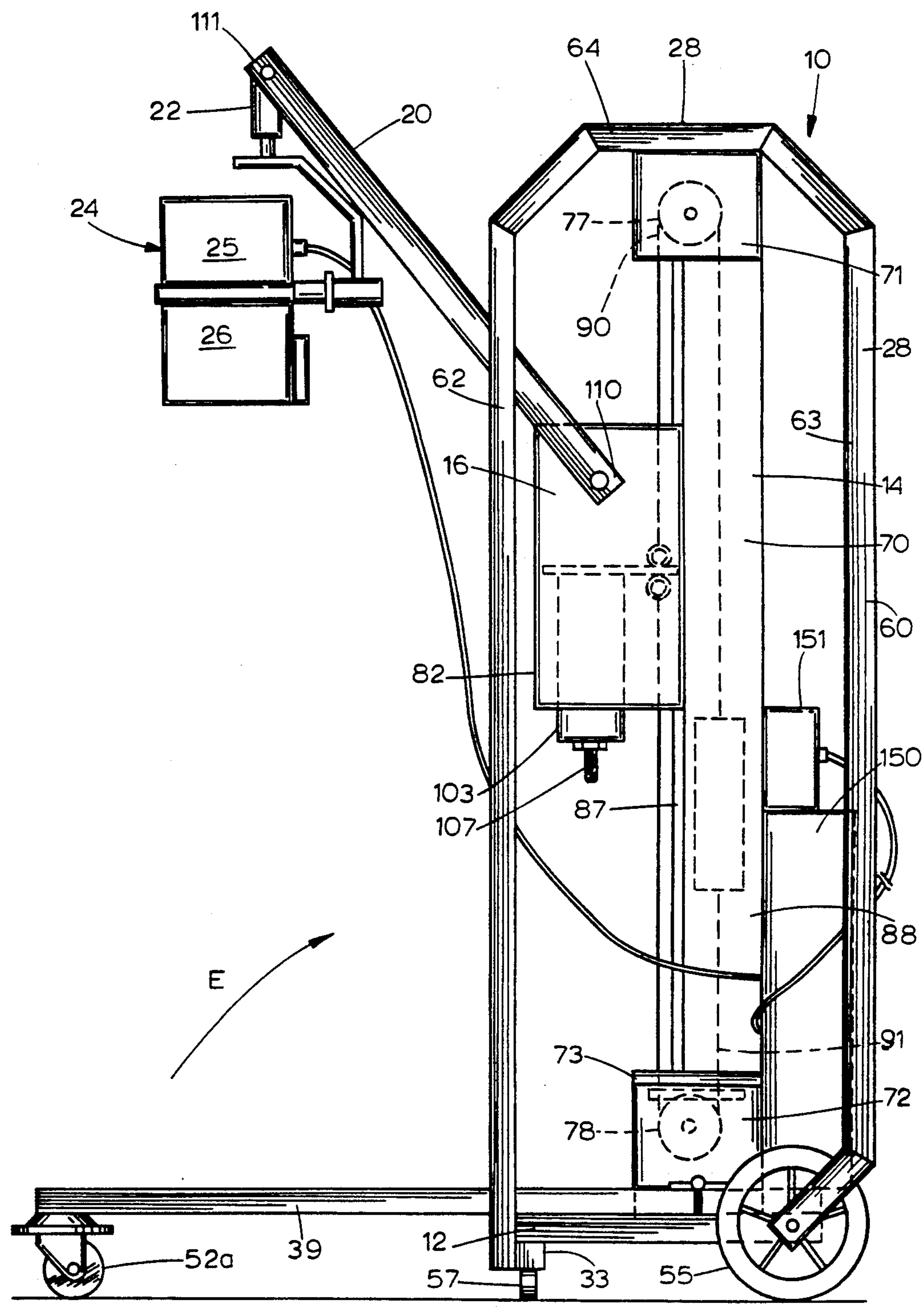
FIG. 1 shows a view of the right side of one embodiment of the portable radiographic unit of the present invention with the unit in an open, operative position.
Figure 2:
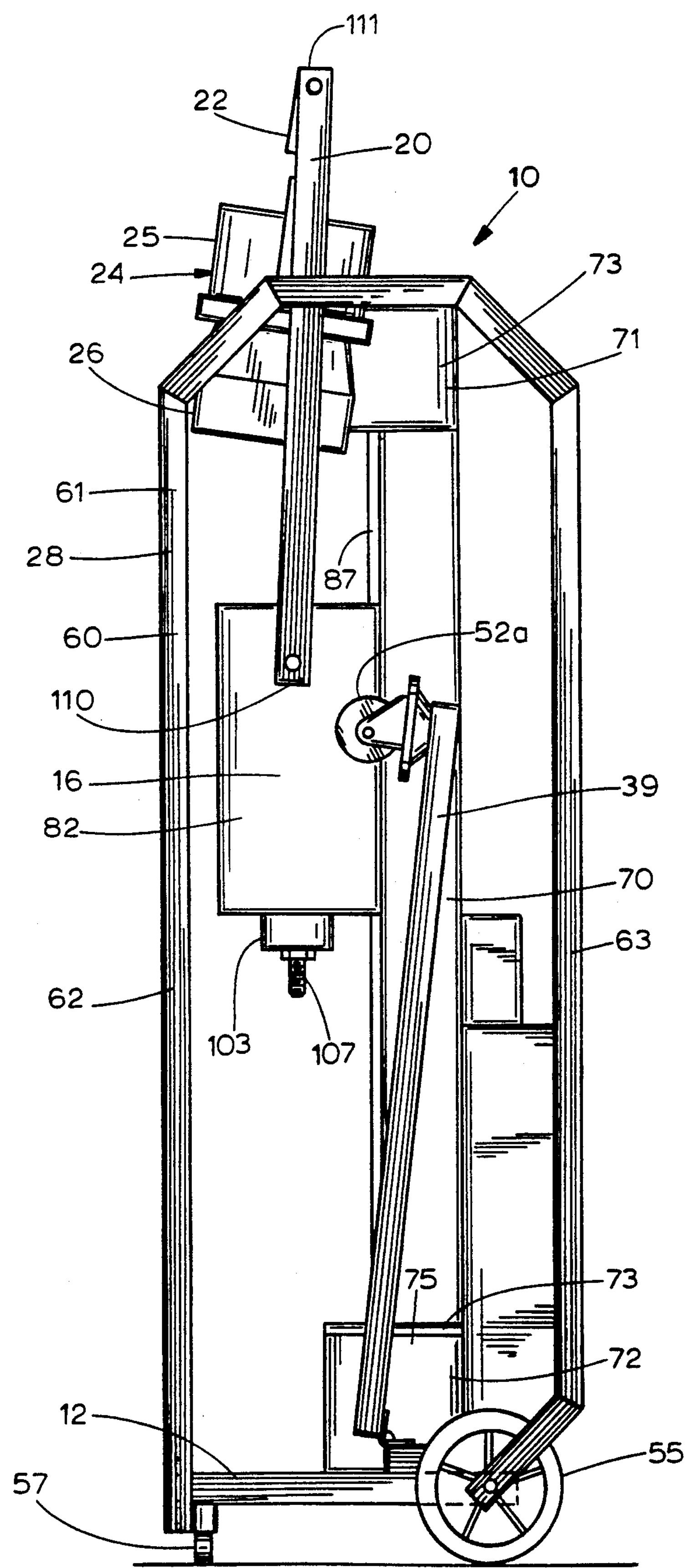
FIG. 2 shows the radiographic unit of FIG. 1 with the unit in a collapsed, inoperative position.
Figure 3:
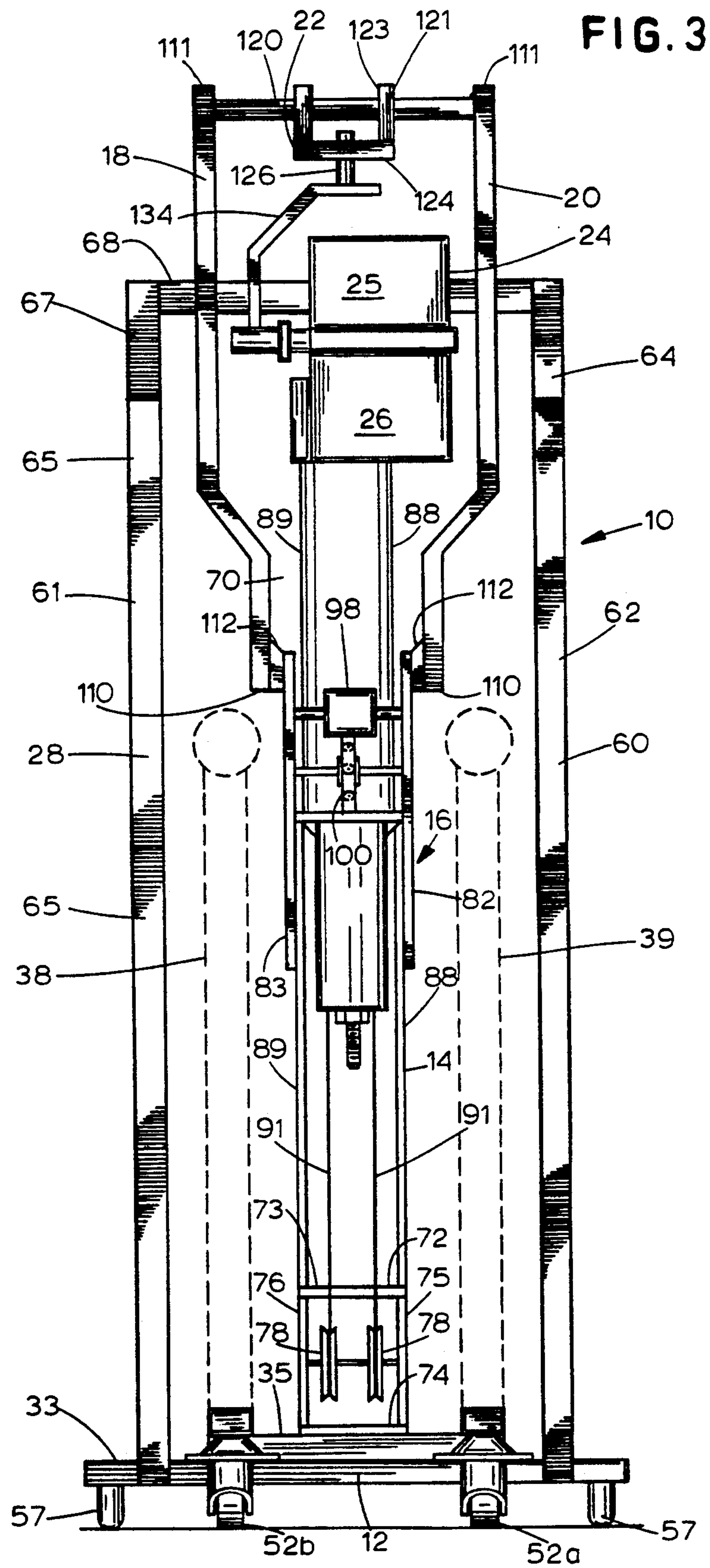
FIG. 3 shows a front view of the radiographic unit of FIG. 2 in a collapsed position.

Referring to the drawings, FIGS. 1-3 show a radiographic device 10 which includes base assembly 12 and column assembly 14 connected to base assembly 12. Carriage assembly 16 moves vertically along at least a portion of column assembly 14. One end of each arm extension member 18, 20 is connected to assembly 16. A disconnectable assembly 22 is connected to the outboard ends of arm extension members 18, 20 and a radiographic head 24 is releasably connected to assembly 22. As used herein, radiographic head is meant to include a power source 25 and an associated collimator 26 which is attached to and depends from the power source. Roll bar assembly 28 is disposed about the front, back and sides of unit 10.

Figure 4:
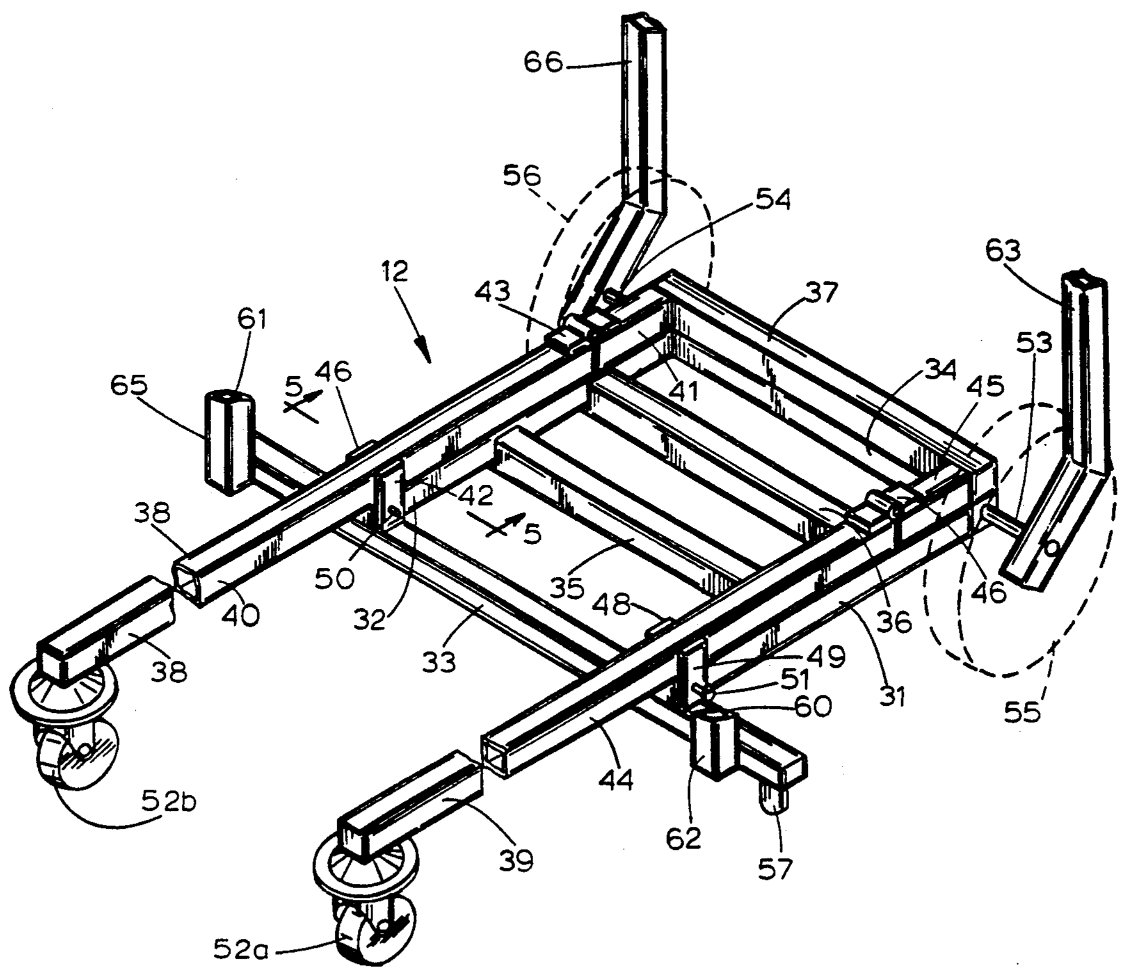
FIG. 4 shows a fragmentary perspective view of the base assemble and leg extension members of the radiographic unit in an open position.

As seen more clearly in FIG. 4, the main frame assembly of the radiographic device includes base assembly 12 and roll bar assembly 28. Base assembly 12 comprises parallel frame members 31, 32, the ends of which are attached by welding or by suitable fasteners to spaced parallel frame members 33, 34. Frame members 35, 36 lie intermediate and, preferably, parallel to frame members 33, 34, members 35, 36 also being fixed by welding or other suitable fasteners to frame members 31, 32.

Top frame member 37 is disposed upon bottom frame member 34; however, if desired, frame members 34, 37 can be formed as a single member.

Leg extension members 38, 39 extend outwardly from base assembly 12. When the unit is in an open, operative position, leg extension member 38 seats on top of frame member 32 whereas leg extension 39 seats on top of frame member 31. Leg extension members 38, 39 each include two portions connected together by a suitable hinge means. Specifically, leg extension member 38 includes portions 40, 41 connected together by hinge means 43 whereby leg extension portion 40 pivots about hinge 43 in the direction of arrow E (FIG. 1). Similarly, leg extension member 39 includes portions 44, 45 connected together by hinge 46 whereby leg extension portion 44 pivots about hinge 46 in the direction of arrow E.

Figure 5:
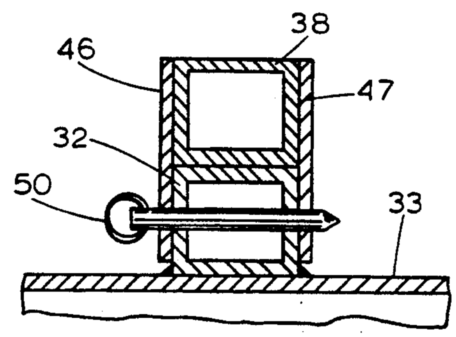
FIG. 5 shows a front section view taken along lines 5—5 in FIG. 4 illustrating the means for releasably locking the leg extension members to the base assembly.

If desired, leg extension members 38, 39 can be releasably secured to frame members 31, 32. Plates 46, 47 are fixed to and depend from leg extension member 38 while plates 48, 49 are fixed to and depend from leg extension member 39. Each depending portion of a plate has an opening therein as do frame members 31, 32 (see, e.g., FIG. 5). Pins 50, 51 are adapted to be inserted in the respective openings as illustrated in FIGS. 4 and 5 thereby anchoring leg extension members 38, 39 to frame members 31, 32.

Wheel 52*a* is connected to the outboard end of leg extension member 39, while wheel 52*b* is connected to the outboard end of leg extension member 38 in a conventional manner such that wheels 52*a*, 52*b* swivel 360° about a vertical axis. An elastomeric footguard is disposed about each wheel 52*a* and 52*b*.

Referring to the opposite ends of leg extension members 38, 39, shafts 53, 54 extend outwardly from the respective ends of frame member 37. Wheel 55 is disposed for rotation about shaft 53 while wheel 56 is disposed for rotation about shaft 54.

It will be noted that the ends of base frame member 33 project outwardly a short distance beyond base frame members 31 and 32. A stop member 57 made of a suitable elastomeric material is connected in a conventional manner to and depends from each end of frame member 33.

Roll bar assembly 28 is fastened or otherwise joined to base assembly 12 at the location of frame member 33 and shafts 53, 54. Roll bar assembly 28 comprises two rail members 60, 61 (FIGS. 1-4). Each rail member has somewhat of an inverted U-shape. Rail member 60 includes rail legs 62, 63 joined together by arcuate-shaped segment 64 while rail member 61 comprises rail legs 65, 66 joined by arcuate-shaped segment 67. Reinforcing bar 68 (FIG. 3) connects arcuate-shaped segments 64, 67. The outboard ends of rail legs 62 and 65 are connected to frame member 33 while the inclined outboard ends of rail legs 63, 66 are disposed on and connected to shafts 53, 54 respectively.

Base assembly 12 and roll bar assembly 28 serve as a main frame assembly to enclose and confine the components of the portable radiographic unit when the unit is in a collapsed, inoperative position thereby protecting the enclosed unit components during transit from contact with adverse elements. Further, unit 10 can be stored in several positions. For example, the unit can rest either on rail legs 62 and 65 or on rail legs 63, 66 and wheels 55, 56. Additionally, although in a less preferred manner, the unit can be transported or stored by resting unit 10 on rail legs 62, 63, frame member 33 and wheel 55 or rail legs 65, 66, frame member 33 and wheel 56.

Seated on base assembly 12 is column assembly 14 which includes a hollow column member 70. Pulley box 71 is located at the top end of column member 70 while pulley box 72 is located at the bottom end of column member 70 (FIGS. 1, 3). Pulley boxes 71, 72 each include a top plate 73, bottom plate 74 and side plates 75, 76. A shaft extends between pulley box side plates 75, 76. A pair of pulleys 77 are mounted for rotation on the shaft in pulley box 71 and a pair of pulleys 78 are mounted for rotation on the shaft in pulley box 72.

Located within vertical hollow column member 70 is counterweight 80 (FIG. 6) which is adapted to travel upwardly and downwardly within column member 70. Counterweight 80, as will be described hereafter, serves as a component for counterbalancing the vertical movement and positioning of carriage assembly 16.

Figure 6:
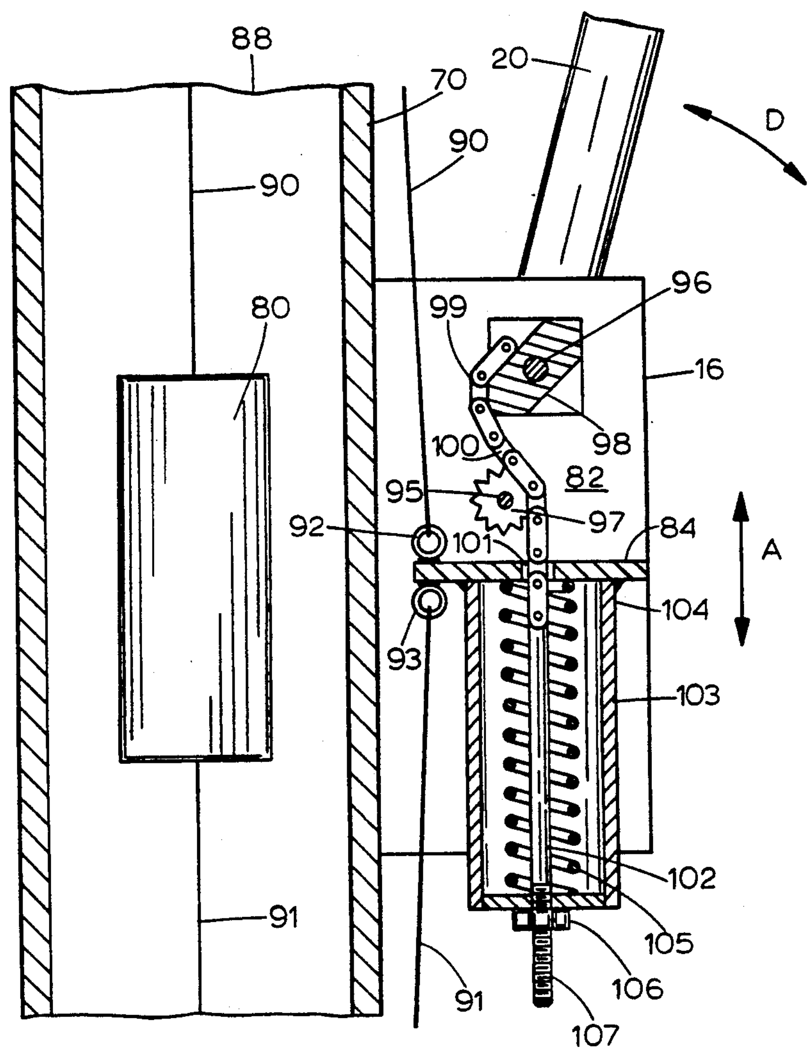
FIG. 6 shows a fragmentary, section view of the left side of the unit of the embodiment of FIG. 1 showing a counterbalancing means for maintaining the carriage assembly in a selected position relative to the column assembly and a counterbalancing means for maintaining the arm extension members in a selected position relative to the carriage assembly.
Figure 7:
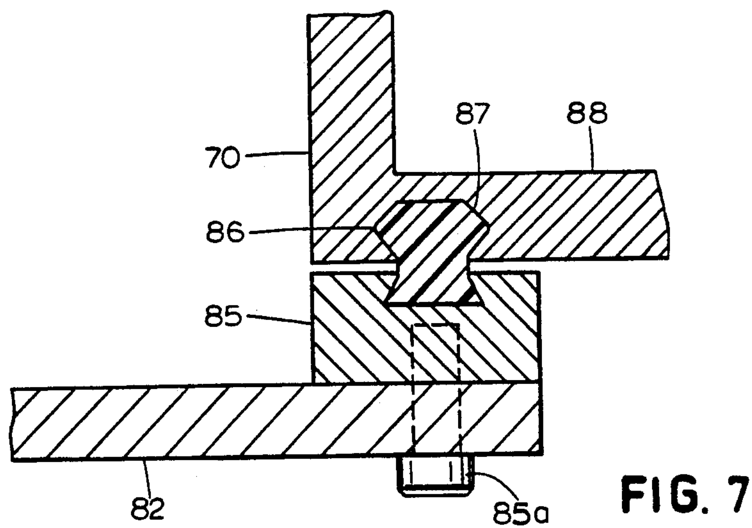
FIG. 7 shows a fragmentary, top section view taken along lines 7—7 in FIG. 1 showing a slide bearing element connected to the carriage assembly and disposed to travel in a vertical track located in the column assembly.

Carriage assembly 16, as seen for example in FIG. 6, includes a pair of spaced vertical carriage plates 82, 83 and horizontal carriage plate 84 connected to plates 82, 83 by welding or the like. One or more spacer bars 85 (F&G. 7) are fastened by a bolt fastening member 85*a* to the inner walls of plates 82, 83 and a resinous bearing element 86 is disposed within a groove formed in spacer bar 85. A recessed track 87 extends vertically along each of the walls 88, 89 of vertical column member 70. The bearing elements 86 slide within the column member tracks whereby carriage assembly 16, as shown by arrow A in FIG. 6, travels vertically relative to column member 70.

As also seen in FIG. 6, a first and second set of pulley wires 90, 91 connect counterweight 80 to carriage assembly 16. Specifically, one end of each pulley wire 90 is releasably connected to mounting hook 92 attached to the top of carriage plate 84. Each pulley wire 90 extends upward over pulley 77 and then downward through an opening in bottom pulley box wall 74 where the remaining wire end is releasably connected by any suitable means to counterweight 80. Similarly, one end of each pulley wire 91 is releasably connected to mounting hook 93 which is mounted on the bottom of carriage plate 84. Each pulley wire 91 extends downward where it passes over pulley 78 and then extends upward through an opening in pulley box wall 73 where it is releasably connected by any suitable means to the bottom of counterweight 80.

It can be appreciated that the weight of counterweight 80 will depend upon the weight of carriage assembly 16 and the loads acting upon assembly 16 when unit 10 is either in an open, operative or a closed, inoperative condition. The desired weight can be selected by a person of ordinary skill in the art bearing in mind that carriage assembly 16 must be balanced so that it will remain in a particular selected position. The weight of counterweight 80 is based upon the weight of carriage assembly 16, arm extension members 10, 11, radiographic head 24, disconnect assembly 22, plus any frictional force generated in the course of movement of carriage assembly 16 in carriage tracks 87. Various weights can be selected until the end result is achieved, i.e., the desired balancing which permits manual or hand movement of carriage assembly 16 and the maintaining of assembly 16 in a selected position.

Carriage assembly 16 further includes a first sprocket shaft 95 and a second pinch box shaft 96 which are positioned above horizontal carriage plate 84. Each shaft is mounted in any suitable manner for rotation in openings located in carriage plates 82, 83. Sprocket 97 is mounted for rotation in the middle of shaft 95. Pinch box 98 is releasably attached or pinched to the middle of rotatable shaft 96. Box 98 includes a cam surface 99 and an attaching means for attaching one end of chain 100 to pinch box 98. Any suitable connection means can be employed to releasably connect chain 100 to pinch box 98.

As seen more clearly in FIG. 6, chain 100 extends from pinch box 98 and passes over cam surface 99 and chain sprocket 97 following which it passes through opening 101 located in horizontal carriage plate 84. The remaining end of chain 100 is fastened by any suitable means to one end of elongated rod 102.

Rod 102 is disposed within a tubular member 103 having an end 114 fixed by welding to the bottom of horizontal carriage plate 84. Compression spring 105 is positioned over chain 102 with its upper end seated against the bottom surface of horizontal carriage plate 84. Washer 106 having an external diameter slightly less than the internal diameter of tubular member 103 and an inner diameter slightly larger than the external diameter of rod 102, is seated against the remaining end of compression spring 105. Nut 106 is threaded onto the outboard threaded end 107 of chain rod 102.

Arm extension members 18, 20 each have two ends 110 and 111. An arm extension mounting member 112 (FIG. 3) is fixed to each arm extension member 18, 20 at end 110. Mounting member 112 fixedly mounts arms 18, 20 on rotatable shaft 96 located in carriage assembly 16.

Disconnectable assembly 22 is connected to arm extension members 18, 20 at their respective ends 111. Assembly 22, as shown in more detail in FIGS. 3 and 8, comprises a shaft 120 fixedly connected to ends 111 of spaced arm extension members 18, 20. A U-shaped yoke 121 is positioned on and is adapted to rotate about shaft 120, the yoke being retained in position on shaft 120 by any conventional keying means. If desired, the shaft also can be installed to rotate within the openings in arm extension members 18, 20 and yoke 121 can be fixed to the shaft. Yoke 121 consists of arms 122, 123 which terminate into base 124 having an opening 125.

Disconnect shaft 126, has an annular recess 127. One end of shaft 126 is adapted to pass through yoke base Opening 125. In assembly, horizontal yoke base openings 128, 129 are aligned with annular recess 127 in disconnect shaft 126 and disconnect pins 130, 131 are inserted in the aligned openings to lock disconnect shaft 126 to yoke 121 whereby shaft 126 can rotate 360° in the direction shown by arrow B in FIG. 8.

Hanger 134 is fixed to and depends from disconnect shaft 126. Hanger 134 includes horizontal hanger section 135, inclined hanger section 136 and vertical hanger section 137, the latter terminating in hanger end 138. Hanger end 138 is fixed by welding or other suitable means to sleeve 140.

Figure 8:
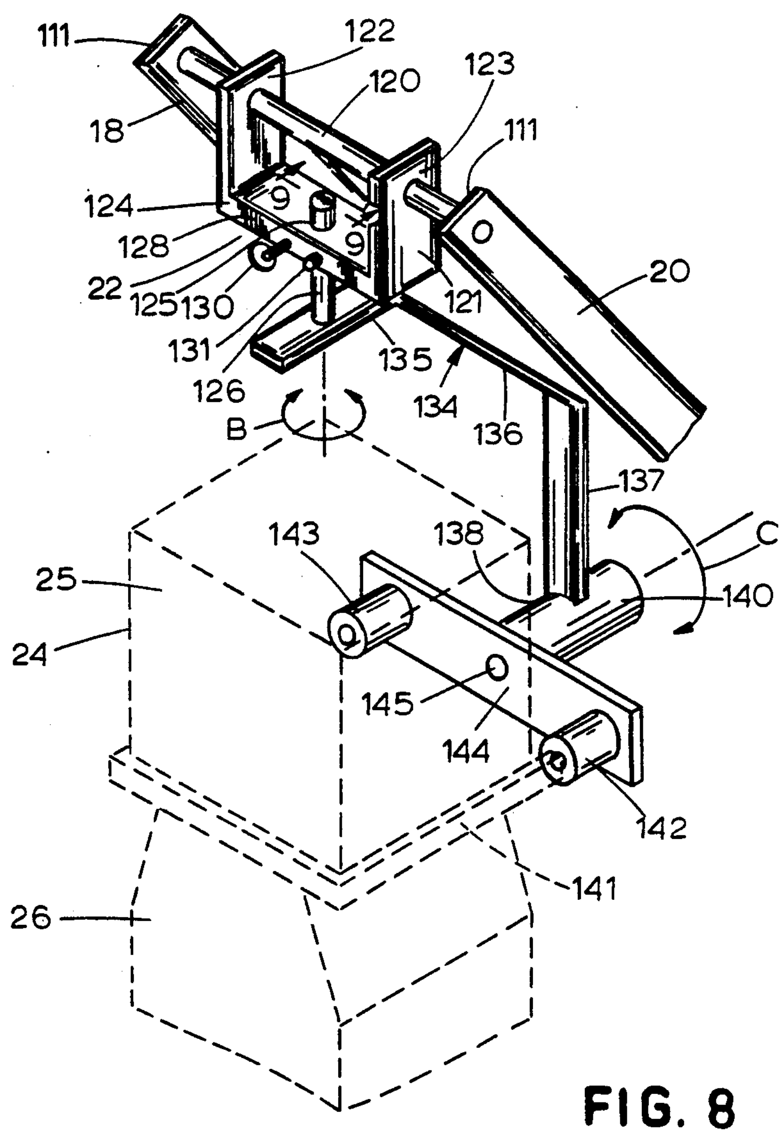
FIG. 8 shows a fragmentary, perspective view of the radiographic head which comprises an x-ray power source and collimator, releasably connected to a disconnect assembly located at the outboard ends of the arm extension members.
Figure 9:
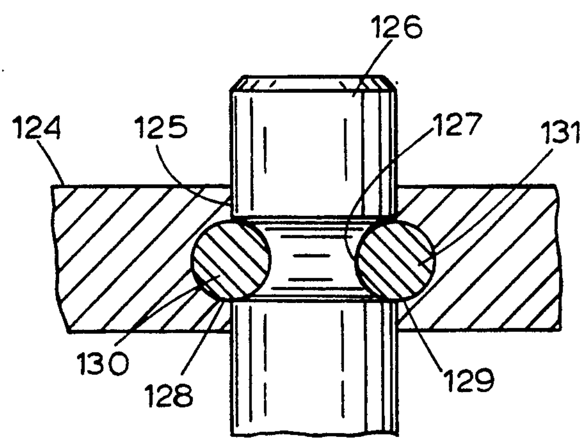
FIG. 9 shows a front section view taken along lines 9—9 in FIG. 8 showing the radiographic unit disconnect device.
Figure 10:
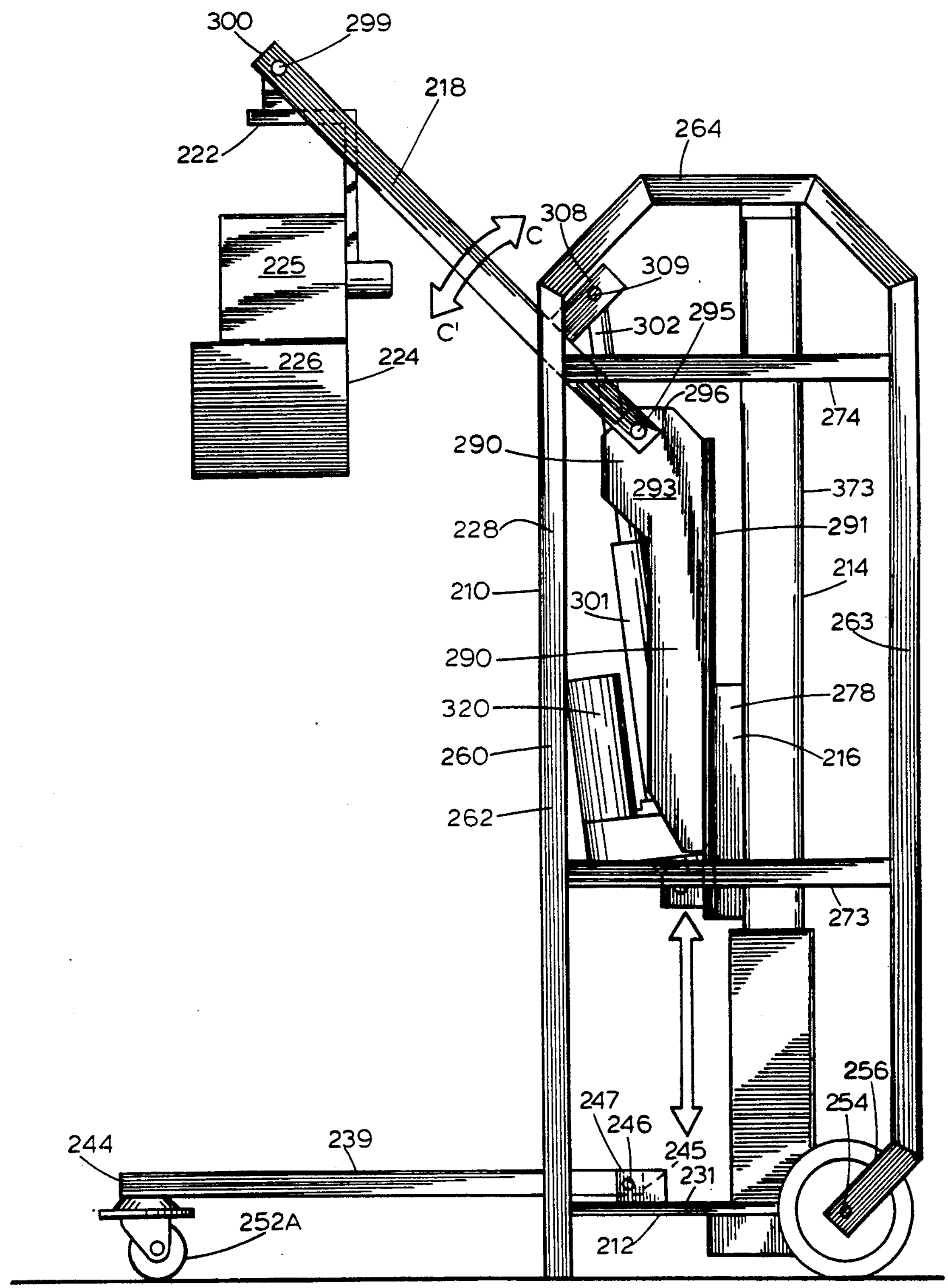
FIG. 10 shows a view of the right side of a second embodiment of the portable radiographic unit of the present invention with the unit in an open, operative position.

Radiographic head 24, which comprises a suitable power source 25 and collimator 26, is disposed within a conventional mounting bracket 141 illustrated in phantom lines in FIG. 8. Bracket 141 is connected to tubular mounting members 142, 143 which, in turn, are fixed to mounting bar 144. Bar 144 has shaft 145 fixed to it which is adapted to be releasably fastened by conventional fastening means within sleeve 140 whereby radiographic head 24 can rotate with shaft 145 in the direction shown by the arrow C in FIG. 8.

When arm extension members 18, 20 having radiographic head 24 located at ends 111 thereof are moved in the direction of arrow D in FIG. 6, spring 105 will either compress or expand to produce a variable spring loading sufficient to counterbalance the loading generated for a particular position for radiographic head 24. For example. If arm extension members 18, 20 are moved downward in the direction indicated by the arrow D in FIG. 6, shaft 96 rotates which, in turn, causes pinch box 98 to rotate thereby moving cam surface 99 to a position which causes chain 100 to move upwardly. As chain 100 and rod 102 move upward, they cause spring 105 to compress thereby creating an increased spring force to offset the increased loading generated as radiographic 24 is moved downward such that a counterbalancing system is employed as the arm extension members 18, 20 pivot about carriage assembly 16 on shaft 96.

In use, leg extension members 38, 39 are pivoted downward in the direction opposite to arrow E (FIG. 1). If desired, legs 38, 39 can be locked in position by locking pins 50, 51. Device 10 can be moved easily by an operator to a desired position relative to a patient or examining table. This ease of operation is particularly appreciated when an operator is on the side of a patient or table opposite the side where device 10 is located. The operator can reach across the table without excessive difficulty and orient the device to the desired location merely by pulling or pushing on rail members 60, 61.

Carriage assembly 16 can be elevated or lowered to the desired position by pushing upwardly or downwardly on assembly 16. Once in a selected position, assembly 16 will remain in that position due to the first counterbalancing means involving the pulley and counterweight arrangement heretofore described.

Similarly, arm extension members 18, 20 can be pivoted about shaft 96 to a selected location and the radiographic head 24 will remain in the desired position due to the second counterbalancing means associated with carriage assembly 16, pinch box 98, chain 100 and compression spring 105 as previously described.

Preferably, the various frame components are made of extruded anodized aluminum. It is appreciated the unit, if desired, could be fabricated from other materials also.

As seen in FIG. 1, power pack 150 is releasably fastened to the back of column member 70. A remote control box 151 in releasably positioned on top of power pack 150 with cables 152, 153 leading from power pack 150 to the radiographic power source 25 and the remote control device 151.

FIGS. 10–13 show a further embodiment of the invention in which radiographic device or unit 210 includes base assembly 212 and column assembly 214 connected to the base assembly by any suitable means such as welding or the like. Carriage assembly 216 moves vertically along at least a portion of column assembly 214. One end of each arm extension member 218, 220 is pivotally connected to assembly 216. A disconnectable assembly 222 is connected to the outboard ends of arm extension members 218, 220 and a radiographic head 224, which includes power source 225 and an associated collimator 226, i-- releasably connected to assembly 222. Roll bar assembly 228 is disposed about the front, back and sides of unit 210.

The main frame assembly of the radiographic device of the embodiment shown in FIGS. 10–13 includes base assembly 212 and roll bar assembly 228. Base assembly 212 comprises a base plate 231 and frame members 232, 233 attached to base plate 231 by welding or by suitable fasteners.

Figure 12:
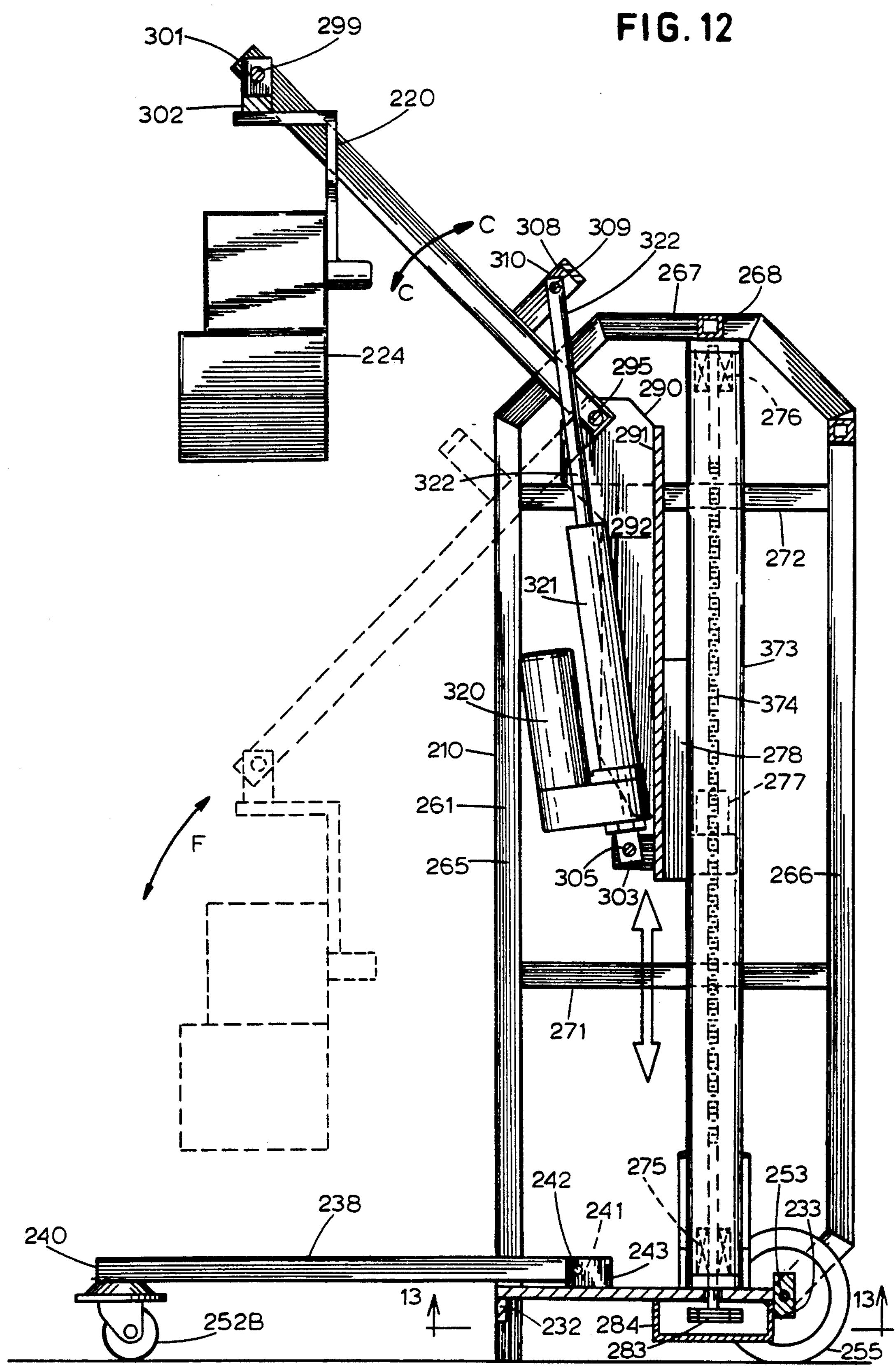
FIG. 12 shows the radiographic unit of FIG. 10 taken along lines 12—12 in FIG. 11; and, FIG. 13 shows a fragmentary, plan section view taken along lines 13—13 in FIG. 12 showing a drive motor shaft connected to a rotatable screw shaft which extends along the length of a column assembly.

Leg extension members 238, 239 extend outwardly from base assembly 212. When the unit is in an open, operative position, leg extension members 238, 239 seat on top of base plate 231. Leg extension member 238 comprises one tubular member having ends 240, 241. End 241 is connected by a pivot pin means 242 mounted in block 243, which is fixed in any suitable fashion to base plate 231, whereby leg extension member 238 is adapted to pivot about pivot pin 242 in the direction of the arrow F (FIG. 12). Similarly, leg extension member 239 comprises a tubular member having ends 244, 245. End 245 also is connected by a pivot pin means 246 mounted in block 247, which also is fixed to base plate 231, whereby leg extension member 239 is adapted to pivot about pivot pin 246 in the direction of arrow F.

Wheel **252*a* is connected to the outboard end of leg extension member 239 while wheel 252*b* is connected to the outboard end of leg extension member 238 in a conventional manner such that wheels 252*a*, 252*b* swivel 360° about a vertical axis. An elastomeric footguard is disposed about each wheel 252*a*, 252*b***.

Shafts 253, 254 extend outwardly from respective ends of frame member 233. Wheel 255 is disposed for rotation about shaft 253 while wheel 256 is disposed for rotation about shaft 254.

Roll bar assembly 228 is fastened or otherwise joined to base assembly 212 at the location of frame member 232 and shafts 253, 254. Roll bar assembly 228 comprises two rail members 260, 261. Each rail member has somewhat of an inverted U-shape. Rail member 260 includes rail legs 262, 263 joined together by arcuate-shaped segment 264. Rail member 261 comprises rail legs 265, 266 joined by arcuate-shaped segment 267. Reinforcing bar 268 (FIGS. 11, 12) connects arcuate-shaped segments 264, 267. The outboard ends of rail legs 262 and 265 extend below base plate 231 (FIG. 10) and each leg is connected to frame member 232 by any suitable means such as welding plates 269, 270 which are welded to frame members 232, base 231 and legs 262, 265. The inclined outboard ends of rail legs 263, 266 are disposed on and connected to shafts 254, 253 respectively.

If desired, additional spaced reinforcing members 271, 272 connect members 265, 266 while spaced reinforcing member 273, 274 connect members 262, 263.

Figure 11:
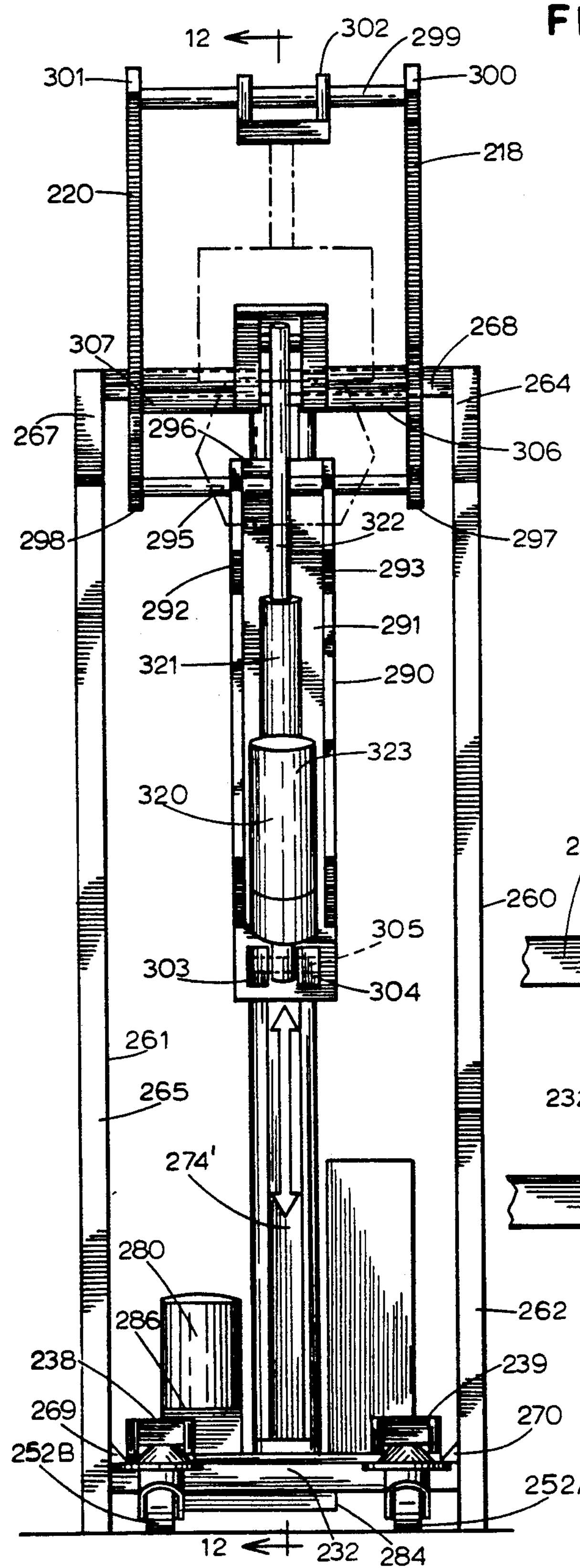
FIG. 11 shows a front view of the radiographic unit of FIG. 10 in a collapsed position.
Figure 13:
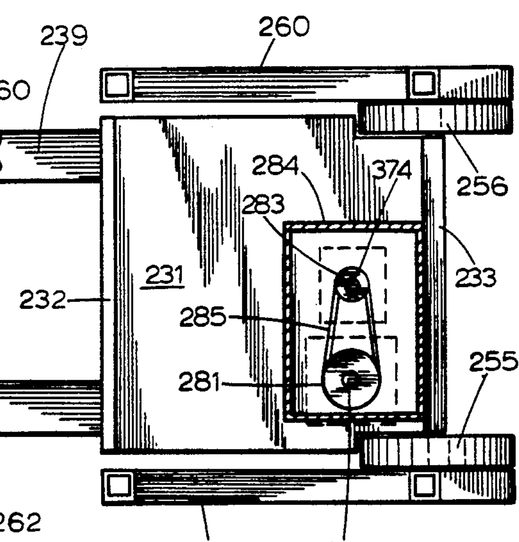

Base assembly 212 and roll bar assembly 228 serve as a main frame assembly to enclose and confine the components of the portable radiographic unit 210 when the unit is in a collapsed, inoperative position thereby protecting the enclosed unit components during transit from contact with adverse elements. As illustrated in FIGS. 11 and 12, the arm extension members 218, 220 and head assembly 224 can be moved downward whereby head assembly 224 is parked over base assembly 212 and within the roll bar assembly 228. Further, unit 210 can be stored in several positions. For example, the unit can rest either on rail legs 262 and 265 or on rail legs 263, 266 and wheels 255, 256.

Seated on base assembly 212 is a column assembly 214 which includes a hollow column member 373. The top end of column assembly 214 is fastened to cross bar 268. The column is open at 274'(FIG. 11).

A rotatable, threaded shaft 374, which extends along the length of column member 373, is journaled at each of its ends in bearings 275, 276. A carriage 277 is connected to and adapted to travel along the length of threaded shaft 374 whereby the carriage can travel vertically up and down the length of the column 373. A saddle 278 is attached to carriage 277 by any suitable means. Saddle 278 is adapted to travel along the vertical length of column 373 in the area of opening 274' (FIG. 11).

Drive motor 280 is seated on base plate 231. Drive pulley 281 is disposed on motor shaft 282. Pulley 283 in pulley box 284 is disposed at one end of screw shaft 374. Belt 285 connects pulleys 281, 283 such that, upon actuation of motor 280, screw shaft 374 rotates thereby permitting carriage 277 and saddle 278 to travel vertically along the length of column 373. A suitable motor control, illustrated at 286, actuates motor 280 to permit carriage 277 to travel to a desired position on shaft 374.

A threaded shaft drive and motor control system which can be adapted for use in the present invention is available from Warner Electric, South Beloit, Ill., Model No. TS09. B03, SCREW DRIVE, 90 MM, 3' STROKE'. The motor, type 34 R 6 BFCI-W2, is available from Bodine Electric Co., Chicago, Ill. A brake is available from Warner Electric Co., #5151-M0-001 90 VDC, ERS-42. The controller for the motor control system is available from X-Cel X-Ray Corp. referenced to as M-6 Motor Control.

Bracket 290 comprises bracket base 291 and spaced bracket plates 292, 293 extending outward from base 291. Bracket 290 is attached to saddle 278 by any suitable means, such as fasteners, such that saddle 278 and bracket 290 travel together vertically along column assembly 214.

Pivot shaft 295 is connected to bracket plates 292, 293 at the upper end 296 of bracket 290. Arm extension members 218 and 220 each are mounted for rotation in the direction of the arrow "C—C" about shaft 295 at extension member ends 297, 298. Another shaft 299 is connected to extension members 218 and 220 at their respective remaining ends 300, 301.

Detachable head assembly 222 is dependently mounted from yoke 302 which is disposed to rotate on shaft 299.

As seen in FIGS. 11 and 12, spaced mounting members 303, 304 are fixedly mounted to and extend outward from bracket base 291. One end of shaft 305 is disposed in mounting member 303 whereas the remaining end of shaft 305 is disposed in mounting member 304. A piston assembly 320 is connected for rotation about shaft 305.

Piston assembly 320 includes piston 321, piston rod 322 and piston drive assembly or actuator 323. A suitable piston assembly or actuator adapted for use in this particular embodiment is available from Warner Electric Co., catalog no. (SPO-05301) #A12-20A5, 12 X L, which is an actuator with a 12 inch stroke.

Referring to FIG. 11, shaft 306 extends inward from extension member 218 and shaft 307 extends inward from extension member 220. The outboard ends of shafts 306, 307 are attached to yoke 308. Shaft 309 is disposed within, yoke 308 and the outboard end 310 of piston rod 322 is mounted for rotation on yoke shaft 309.

As shown for illustration purposes in FIG. 12, as piston rod 322 is drawn inwardly into piston 321, arm extension members 218, 220 and head assembly 224 are pulled downwardly as shown in phantom lines in FIG. 12. One end of the arm extension members 218, 220 pivots about shaft 295, which causes the arm extension members to pivot in the direction of arrow C'.

Conversely, when piston rod 322 is pushed outward from piston 321, the arm extension members 218, 220 pivot about shaft 295 in the direction of arrow C. Controlling the movement of piston rod 322, permits an operator to orient the head assembly 224 in a desired position.

Further, actuation of drive motor 280 permits carriage 277 to travel vertically along column 373 so as to permit head assembly 224 to be oriented vertically relative to a patient.

When it is desired to place unit 210 in an inoperative position, leg extension members 238, 239 are pivoted about shafts 242, 246 where members 238, 239 assume a closed position such as illustrated in FIG. 2.

A suitable radiographic head including the power source and collimator is available as Model M6 from X-Cel X-Ray Corporation, 4220 Waller Drive, Crystal Lake, Ill. 60012. A system available for use as a power source is disclosed in U.S. Pat. No. 5,111,493, the disclosure of which is incorporated by reference herein. The x-ray power source 25 relies on excitation from power pack 150. The power pack is controlled by a remote control device 151. The remote control by virtue of its microprocessor requires minimal maintenance. Power pack 150 utilizes energy storage in the form of large capacitors which are then employed in a controlled discharge via a switching regulator to power x-ray power source 25. The modular construction and circuitry are selected to allow for minimum weight and power consumption and also to provide for ease of repair. Whereas conventional x-ray equipment requires large currents from the power line, radiographic unit of the present invention equipment requires only a small percentage of the conventional power input.

While the unit may be of various sizes, it is preferred units 10 and 210 be relatively compact and have a 21", (±2") width, 21", (±2") depth and 61½", (±1") height. The weight of the unit is between 200 and 250 pounds and preferably 200 pounds.

While one or more embodiments of the invention have been herein illustrated and described in detail, it will be understood that modifications and variations thereof may be effected without departing from the spirit of the invention and the scope of the appended claims.

What is claimed is:

1. A portable radiographic unit adapted to be positioned in an open, operative position and a closed position, said unit comprising:

a base assembly including means for permitting manually movement of said unit from one position to another;

a pair of spaced leg extension members pivotally connected to said base assembly and including second means connected to said leg extension members for moving said unit from one position to another;

a column assembly extending upward from and connected to said base assembly;

a carriage assembly connected to and positioned for travel along the length of said column assembly;

a pair of spaced arm extension members, each arm extension member having a first end and a second end, said first ends being pivotally connected to said carriage assembly whereby said arm extension members pivot about said carriaqe assembly;

a disconnectable assembly attached to said second ends of said arm extension members; and, a radiographic head releasably connected to said disconnectable assembly.

2. A portable radiographic unit in accordance with claim 1 and further including a first counterbalancing means for maintaining said carriage assembly in a selected position on said column assembly.

3. A portable radiographic unit in accordance with claim 2 and further including a second counterbalancing means for maintaining said pivotable arm extension members in a selected position relative to said carriage assembly.

4. A portable radiographic device in accordance with claim 3 and further including a roll bar assembly means for protecting said base assembly, column assembly and carriage assembly when said unit is in a closed position and said leg extension members are positioned contiguous to said column assembly.

5. A portable radiographic unit in accordance with claim 4 wherein said roll bar assembly comprises a pair of spaced rail members, each of said rail members being fastened to said base assembly.

6. A radiographic unit in accordance with claim 5 where said rail members each include a pair of spaced legs having two ends, one of said leg ends terminating in an arcuate-shaped section and the remaining leg end being connected to said base assembly.

7. A radiographic unit in accordance with claim 6 and further including a reinforcing bar connecting said arcuate-shaped sections of said rail members.

8. A radiographic unit in accordance with claim 1 wherein said base assembly includes a first pair of spaced parallel base members and a second pair of spaced parallel base members connected perpendicular to said first pair of base members.

9. A radiographic unit in accordance with claim 8 and further including at least one intermediate base member positioned between said second pair of members and connected to said first pair of base members.

10. A radiographic device in accordance with claim 1 wherein said column assembly comprises a hollow column having two ends;

a first pulley box located at one end of said column and a second pulley box located at said remaining column end.

11. A radiographic unit in accordance with claim 10 wherein said column includes at least one track disposed thereon;

means connected to said carriage assembly for traveling in said column track whereby said carriage assembly is adapted to travel along at least a portion of the length of said column.

12. A radiographic unit in accordance with claim 11 wherein a first counterbalancing means includes at least one rotatable pulley disposed in each of said first and second pulley boxes, a counterweight disposed within said hollow column, means for mounting pulley wires on said carriage assembly and said counterweight, at least one pulley wire connected to said counterweight and to said carriage assembly and passing over said pulley an said first pulley box, and, at least another pulley wire connected to said counterweight and to said carriage assembly and passing over said pulley an said second pulley box.

13. A radiographic unit in accordance with claim 3 wherein said second counterbalancing means includes means for pivotally connecting one end of said arm extension members about said carriage assembly;

a spring assembly means including means for connecting said spring to said arm extension members;

means for maintaining said spring assembly on said carriage assembly, and means acting on said spring means when said radiographic head is pivoted to vary the force acting on said spring means.

14. A portable radiographic unit in accordance with claim 13 wherein said second counterbalancing means includes a chain having two ends;

a pinch box having a cam face connected to a rotatable shaft disposed on said carriage assembly;

a first chain end connected to said pinch box and said chain extending over said cam face;

a rod connected to said second chain end;

a compression spring disposed about said rod; and, means responsive to movement of said arm extension members acting on said spring by movement of said rod relative to said spring.

15. A portable radiographic unit in accordance with claim 1 wherein said disconnectable assembly comprises a shaft connecting the outboard ends of said arm extension members;

a yoke disposed for rotation on said shaft;

a disconnect shaft releasably connected to said yoke and adapted to rotate 360° about a vertical axis;

a hanger member fixed to said disconnect shaft;

a mounting means disposed for rotation about a horizontal axis on said hanger; and, said radiographic unit being disposed on said mounting means.

16. A portable x-ray unit adapted to be placed in an open or collapsed position, said device comprising:

a base assembly;

a first pair of wheels connected to the base assembly;

a pair of spaced leg extension members having movable means located thereon for assisting and moving said unit;

means connected to said base assembly for permitting manual movement of said unit from one position to another;

each of said leg extension members having a first end pivotally connected to said base assembly and a second outboard end positioned away from said base assembly when said unit is in an open position;

a column assembly extending upward from said base assembly;

a carriage assembly connected to said column assembly, said carriage assembly including means for permitting said carriage assembly to travel along at least a portion of the length of said column assembly;

a pair of spaced arm extension members, each member having first and second ends;

said arm extension member first ends being pivotally connected to and extending outward from said carriage assembly;

an x-ray head; and, means for releasably connecting said x-ray head to said second arm extension member ends.

17. A portable x-ray unit in accordance with claim 16 and further including a first counterbalancing means for maintaining said carriage assembly in a selected position relative to said column assembly.

18. A portable x-ray unit in accordance with claim 17 and further including a second counterbalancing means for maintaining said x-ray head and arm extension members in a selected position.

19. A portable x-ray unit in accordance with claim 18 and further including a roll bar assembly connected to said base assembly.

20. A portable x-ray unit in accordance with claim 19 wherein said roll bar assembly comprises a pair of spaced parallel roll members.

21. A portable x-ray unit in accordance with claim 20 wherein said rail members each have an inverted U-like shape.

22. A portable radiographic unit adapted to be placed in an open or collapsed position, said unit comprising:

a base assembly;

a first pair of wheels connected to the base assembly;

a pair of spaced leg extension members;

means connected to said assembly to permit manual movement of said unit from one position to another;

each of said leg extension members having a first end pivotally connected to said base assembly and a second outboard end positioned away from said base assembly when said unit is in an open position;

rotatable means connected to the outboard ends of each leg extension member;

a column assembly extending upward from said base assembly including a column;

a carriage assembly connected to said column assembly, said carriage assembly including means for permitting said carriage assembly to travel along at least a portion of the length of said column;

a pair of spaced arm extension members, each member having first and second ends;

said arm extension member first ends being pivotally connected to and extending outward from said carriage assembly;

a first means for maintaining said carriage assembly in a selected position along the length of said column;

a second means for maintaining said arm extension members in a selected position relative to said carriage assembly;

a radiographic head;

means for releasably connecting said x-ray head to said second arm extension member ends; and, a roll bar assembly connected to said base assembly, said roll bar assembly surrounding said leg extension members, carriage assembly and column assembly when said unit is in a closed position.

23. A portable unit according to claim 1 or 16 further including means for maintaining said carriage assembly in a selective position along the length of said column assembly.

24. A portable radiographic unit in accordance with claim 1, 16 or 22 in which said carriage assembly includes:

a threaded screw means disposed in said column assembly and extending along at least a portion of the length of said column assembly.

25. A portable radiographic unit in accordance with claim 24 and further including:

a carriage disposed on said screw means and adapted to move vertically along at least a portion of the length of said column assembly;

a saddle connected to said carriage and adapted to travel vertically along said column assembly;

a bracket mounted to said saddle;

a piston assembly including a piston rod pivotally connected to said bracket;

said piston rod having an outboard end;

one end of each of said arm extension members being pivotally connected to said bracket;

a yoke means connected to said arm extension members at a location near said one end of said arm extension members;

said yoke means having a shaft disposed therein;

said outboard end of said piston rod pivotally connected to said yoke means; and, means for actuating said piston rod whereby said arm extension members are pivotable about said bracket.

26. A portable radiographic unit in accordance with claim 25 in which said bracket includes a base and spaced bracket plates extending outward from said bracket base;

a bracket shaft connected to said spaced bracket plates;

one end of each of said arm extension members being connected to said bracket shaft.

27. A portable radiographic unit in accordance with claim 26 and further including a pair of spaced piston mounting plates attached to and extending outward from said bracket base;

a piston assembly mounting shaft connected to said spaced mounting plates; and said piston assembly pivotally connected to said piston mounting shaft.

* * * * *

UNITED STATES PATENT AND TRADEMARK OFFICE

CERTIFICATE OF CORRECTION

PATENT NO. : 5,283,823

DATED : February 1, 1994

INVENTOR(S) : William W. Morris

It is certified that error appears in the above-identified patent and that said Letters Patent is hereby corrected as shown below:

Col. 1, line 8, delete "abandment" and insert --abandonment--;

Col. 2, line 20, delete "he" and insert --the--;

Col. 2, line 48, delete "oar" and insert --bar--;

Col. 3, line 15, delete "assemble" and insert -- assembly--;

Col. 5, line 33, delete "F&G." and insert --FIG.--;

Col. 6, line 26, delete "114" and insert --104--;

Col. 6, line 55, delete "Opening" and insert --opening--;

Col. 7, line 15, following "example" delete ". If" and insert --, if--;

Col. 7, line 57, delete "in" and insert --is--;

Col. 8, line 4, delete "i--" and insert --is--;

Col. 10, line 1, following "within" delete ",";

Col. 10, line 48, delete "height" and insert --height--;

UNITED STATES PATENT AND TRADEMARK OFFICE

CERTIFICATE OF CORRECTION

PATENT NO. : 5,283,823

DATED : February 1, 1994

INVENTOR(S) : William W. Morris

It is certified that error appears in the above-identified patent and that said Letters Patent is hereby corrected as shown below:

Col. 10, lines 61-62, delete "manually" and insert --manual--;

Col. 12, line 5, delete "an" and insert --in--; and

Col. 12, line 8, delete "an" and insert --in--.

Signed and Sealed this

Second Day of August, 1994

Attest:

BRUCE LEHMAN

*Attesting Officer*

*Commissioner of Patents and Trademarks*